US012252507B2

(12) United States Patent
Yang et al.

(10) Patent No.: US 12,252,507 B2
(45) Date of Patent: Mar. 18, 2025

(54) NUCLEIC ACID NANOSWITCH CONSTRUCTION METHODS

(71) Applicants: Children's Medical Center Corporation, Boston, MA (US); President and Fellows of Harvard College, Cambridge, MA (US)

(72) Inventors: Darren Yang, Somerville, MA (US); Eric M. Mulhall, Boston, MA (US); Hongyu Zhao, Boston, MA (US); Andrew Ward, Boston, MA (US); Clinton H. Hansen, Brighton, MA (US); Wesley Philip Wong, Cambridge, MA (US)

(73) Assignees: Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 1043 days.

(21) Appl. No.: 16/466,973

(22) PCT Filed: Dec. 5, 2017

(86) PCT No.: PCT/US2017/064756
§ 371 (c)(1),
(2) Date: Jun. 5, 2019

(87) PCT Pub. No.: WO2018/106721
PCT Pub. Date: Jun. 14, 2018

(65) Prior Publication Data
US 2019/0345193 A1    Nov. 14, 2019

Related U.S. Application Data

(60) Provisional application No. 62/429,905, filed on Dec. 5, 2016.

(51) Int. Cl.
| | | |
|---|---|---|
| *C12Q 1/686* | (2018.01) | |
| *C07H 21/04* | (2006.01) | |
| *C12N 15/11* | (2006.01) | |
| *C12N 15/63* | (2006.01) | |
| *C12Q 1/6804* | (2018.01) | |
| *C12Q 1/6853* | (2018.01) | |
| *G01N 33/542* | (2006.01) | |

(52) U.S. Cl.
CPC .............. *C07H 21/04* (2013.01); *C12N 15/11* (2013.01); *C12N 15/111* (2013.01); *C12N 15/63* (2013.01); *C12Q 1/6804* (2013.01); *C12Q 1/6853* (2013.01); *C12Q 1/686* (2013.01); *C12N 2310/3513* (2013.01); *C12Q 2531/113* (2013.01); *G01N 33/542* (2013.01); *G01N 2458/10* (2013.01)

(58) Field of Classification Search
None
See application file for complete search history.

(56) References Cited

U.S. PATENT DOCUMENTS

| 8,129,119 B2 | 3/2012 | Jarrell et al. |
| 2009/0118140 A1* | 5/2009 | Suzara .................... C40B 40/04 |
| | | 506/17 |
| 2014/0255939 A1 | 9/2014 | Wong et al. |
| 2015/0292007 A1 | 10/2015 | Church et al. |

FOREIGN PATENT DOCUMENTS

| WO | WO 2013/067489 A1 | 5/2013 |
| WO | WO 2016/089588 A1 | 6/2016 |
| WO | WO 2016/164866 A1 | 10/2016 |
| WO | WO 2016/196824 A1 | 12/2016 |
| WO | WO 2017/003950 A2 | 1/2017 |
| WO | WO 2017/139409 A1 | 8/2017 |
| WO | WO 2017/147398 A1 | 8/2017 |
| WO | WO 2017/165585 A1 | 9/2017 |
| WO | WO 2017/165647 A1 | 9/2017 |
| WO | WO 2019/100080 A1 | 5/2019 |

OTHER PUBLICATIONS

Koussa, DNA nanoswitches: a quantitative platform for gel-based biomolecular interaction analysis, Nature Methods, 12(2): 123-126, Feb. 2015. (Year: 2015).*
Ahmad, New FRET primers for quantitative real-time PCR, Anal Bioanal Chem, 387: 2737-2743, 2007. (Year: 2007).*
Wu, Detection of PCR amplicons from bacterial pathogens using microsphere agglutination, Journal of Microbiological Methods, 56, 395-400, 2004. (Year: 2004).*
Meagher, Free-solution electrophoresis of DNA modified with drag-tags at both ends, Electrophoresis, 27, 1702-1712, 2006. (Year: 2006).*
International Search Report and Written Opinion mailed Feb. 26, 2018 for Application No. PCT/US2017/064756.
International Preliminary Report on Patentability mailed Jun. 20, 2019 for Application No. PCT/US2017/064756.
Halvorsen et al., Nanoengineering a single-molecule mechanical switch using DNA self-assembly. Nanotechnology. Dec. 9, 2011;22(49):494005. doi: 10.1088/0957-4484/22/49/494005. Epub Nov. 21, 2011.
Shroff et al., Biocompatible force sensor with optical readout and dimensions of 6 nm3. Nano Lett. Jul. 2005;5(7):1509-14.
Shroff et al., Optical measurement of mechanical forces inside short DNA loops. Biophys J. Mar. 15, 2008;94(6):2179-86. Epub Dec. 7, 2007.
Zadeh et al., NUPACK: Analysis and design of nucleic acid systems. J Comput Chem. Jan. 15, 2011;32(1):170-3. doi: 10.1002/jcc.21596.

* cited by examiner

*Primary Examiner* — Carolyn L Greene
(74) *Attorney, Agent, or Firm* — Wolf, Greenfield & Sacks, P.C.

(57) ABSTRACT

This disclosure provides methods for generating functionalized nanoswitches, as well as the functionalized nanoswitches themselves, and methods of use thereof.

5 Claims, 3 Drawing Sheets

Specification includes a Sequence Listing.

NUCLEIC ACID NANOSWITCH CONSTRUCTION METHODS

RELATED APPLICATIONS

This application is a national stage filing under 35 U.S.C. § 371 of International Patent Application Serial No. PCT/US2017/064756, filed Dec. 5, 2017, entitled "NUCLEIC ACID NANOSWITCH CONSTRUCTION METHODS", which claims the benefit under 35 U.S.C. § 119(e) of U.S. Provisional Application No. 62/429,905 filed Dec. 5, 2016 and entitled "NUCLEIC ACID NANOSWITCH CONSTRUCTION METHODS", the entire contents of both of which are incorporated by reference herein.

REFERENCE TO A SEQUENCE LISTING SUBMITTED AS A TEXT FILE VIA EFS-WEB

The instant application contains a Sequence Listing which was submitted in ASCI format via EFS-Web and is hereby incorporated by reference in its entirety. Said ASCII copy, created on Jun. 5, 2019, is named C123370113US01-SEQ-MAT and is 2,028 bytes in size.

BACKGROUND

DNA nanoswitches are nanoscopic tools made from DNA which can report how molecules behave and interact with high sensitivity. Previous DNA nanoswitch construction has relied on annealing small, synthetic oligonucleotides onto a single-stranded DNA backbone (Halvorsen, 2011). The nanoswitch is functionalized by annealing oligonucleotides linked to molecules of interest (MOI) onto specific regions of the backbone. The remainder of the backbone is annealed to non-functionalized oligonucleotides. The final product contains one, two or more MOIs attached at specific points along its length. These MOIs can then interact with each other, directly or indirectly. The nanoswitch can be used to detect and characterize molecular interactions involving the MOIs in gel-based assay systems or using force spectroscopy.

SUMMARY

This disclosure provides improvements to the basic structure of nucleic acid nanoswitches and to the methods of making such nanoswitches. These improvements, which harness the power of DNA enzymatic reactions, have led to the generation of more stable, less reactive, and ultimately stronger nanoswitches.

This disclosure provides in one aspect a method comprising
  (a) annealing to a single-stranded nucleic acid backbone one or two blocking oligonucleotides lacking a 5' phosphate group, one or two reactive oligonucleotides, each annealing adjacent to the 3' end of one blocking oligonucleotide, and a 5' terminal oligonucleotide, to form a double-stranded, nicked construct,
  (b) capping each of the one or two blocking oligonucleotides with a single ddNTP in the presence of TdT, thereby forming capped blocked oligonucleotides,
  (c) extending the reactive oligonucleotides and the 5' terminal oligonucleotide in the 3' direction in the presence of a polymerase and dNTPs,
  (d) removing the capped blocking oligonucleotides,
  (e) annealing one or two functionalized oligonucleotides to the backbone, each functionalized oligonucleotide conjugated to an agent, and
  (f) ligating the one or two functionalized oligonucleotides to adjacent annealed oligonucleotides to form a fully double-stranded functionalized nucleic acid construct.

Another aspect of this disclosure provides a method comprising
  (a) annealing to a single-stranded nucleic acid backbone one or two capped blocking oligonucleotides lacking a 5' phosphate group and comprising a 3' ddNTP, one or two reactive oligonucleotides, each annealing adjacent to the 3' end of one blocking oligonucleotide, and a 5' terminal oligonucleotide, to form a double-stranded, nicked construct,
  (b) extending the reactive oligonucleotides and the 5' terminal oligonucleotide in the 3' direction in the presence of a polymerase and dNTPs,
  (c) removing the capped blocking oligonucleotides,
  (d) annealing one or two functionalized oligonucleotides to the backbone, each functionalized oligonucleotide conjugated to an agent, and
  (e) ligating the one or two functionalized oligonucleotides to adjacent annealed oligonucleotides to form a fully double-stranded functionalized nucleic acid construct.

Another aspect of this disclosure provides a method comprising
  (a) providing a partially double-stranded nucleic acid construct comprising a nucleic acid backbone annealed to one or two blocking oligonucleotides each lacking a 5' phosphate group and a 3' hydroxyl group, one or two reactive oligonucleotides each positioned adjacent to the 3' end of one blocking oligonucleotide, and a 5' terminal oligonucleotide,
  (b) extending the reactive oligonucleotides and the 5' terminal oligonucleotide in the 3' direction in the presence of a polymerase and dNTPs,
  (c) removing the blocking oligonucleotides,
  (d) annealing one or two functionalized oligonucleotides to the backbone, each functionalized oligonucleotide conjugated to an agent, and
  (e) ligating the one or two functionalized oligonucleotides to adjacent annealed oligonucleotides to form a fully double-stranded functionalized nucleic acid construct.

Another aspect of this disclosure provides a method comprising
  (a) annealing to a single-stranded nucleic acid backbone a plurality of reactive, non-functionalized oligonucleotides each comprising a 5' phosphate and a 3' hydroxyl, and a 5' terminal oligonucleotide, and optionally a 3' terminal oligonucleotide, to form a partially double-stranded nucleic acid construct,
  (b) isothermally annealing one or two functionalized oligonucleotides to the partially double-stranded nucleic acid construct, and
  (c) ligating adjacently-positioned annealed oligonucleotides to each other to form a fully double-stranded functionalized nucleic acid construct.

Another aspect of this disclosure provides a method comprising
  (a) providing a partially double-stranded nucleic acid construct comprising a plurality of reactive, non-functionalized oligonucleotides each comprising a 5' phosphate and a 3' hydroxyl, and a 5' terminal oligonucleotide, and optionally a 3' terminal oligonucleotide, annealed to a nucleic acid backbone, (b) isothermally annealing one or two functionalized oligonucleotides to the partially double-stranded nucleic acid construct, and (c) ligating adjacently-positioned annealed oligonucleotides to each other to form a fully double-stranded functionalized nucleic acid construct.

Another aspect of this disclosure provides a method comprising (a) amplifying three or more sequences from a template nucleic acid, thereby generating three or more double-stranded nucleic acid fragments, wherein a first fragment is cleavable by a first enzyme to yield a first 5' overhang, a second fragment is cleavable by the first enzyme and a second enzyme to yield a second 5' overhang and a second 3' overhang, and a third fragment is cleavable by the second enzyme to yield a third 5' overhang, and wherein one, two or three of the fragments is functionalized or comprises a functionalization point, (b) cleaving each fragment with its respective restriction enzyme thereby yielding fragments with 5' and/or 3' overhangs, (c) optionally functionalizing fragments comprising a functionalization point, and (d) combining the fragments in the presence of a ligase, thereby forming a fully double-stranded functionalized nucleic acid construct.

Another aspect of this disclosure provides a method comprising (a) amplifying three or more sequences from a template nucleic acid, thereby generating three or more double-stranded nucleic acid fragments, wherein a first fragment is cleavable by a first enzyme to yield a first 5' overhang, a second fragment is cleavable by the first enzyme and a second enzyme to yield a second 5' overhang and a second 3' overhang, and a third fragment is cleavable by the second enzyme to yield a third 5' overhang, and wherein one, two or three of the fragments is functionalized or comprises a functionalization point, (b) cleaving each fragment with its respective restriction enzyme thereby yielding fragments with 5' and/or 3' overhangs, (c) combining the fragments in the presence of a ligase, thereby forming a fully double-stranded nucleic acid construct, and (d) optionally functionalizing fully double-stranded nucleic acid construct at the functionalization point, thereby forming a fully double-stranded functionalized nucleic acid construct.

Another aspect of this disclosure provides a method comprising (a) amplifying a sequence from a template nucleic acid using a forward and a reverse primer, thereby generating a double-stranded nucleic acid fragment, wherein the forward and the reverse primers is each functionalized or comprises a functionalization point, and (b) functionalizing the double-stranded nucleic acid fragment using the functionalization points from the forward and reverse primers, thereby forming a fully double-stranded functionalized nucleic acid construct.

Another aspect of this disclosure provides a method comprising (a) restriction enzyme digesting a plasmid to yield a double-stranded nucleic acid having non-complementary sticky ends and having a length of at least 500 bases, (b) ligating, in the presence of a ligase, to each sticky end of the double-stranded nucleic acid (i) a functionalized oligonucleotide comprising an MOI (or agent) or (ii) an oligonucleotide comprising a functionalization point, and then conjugating an MOI (or agent) to the functionalization point, wherein the oligonucleotides of (i) and (ii) each comprise one blunt end and one sticky end, thereby forming a fully double-stranded functionalized nucleic acid construct.

Another aspect of this disclosure provides a method comprising annealing to a single-stranded nucleic acid backbone two or more functionalized oligonucleotides, thereby forming a partially double-stranded functionalized nucleic acid construct. In some embodiments, the partially double-stranded functionalized nucleic acid construct is at least 1%, 2%, 3%, 4%, 5%, 6%, 7%, 8%, 9%, 10%, 20%, 30%, 40%, 50%, or more double-stranded.

Another aspect of this disclosure provides a method comprising (a) contacting any of the foregoing fully double-stranded functionalized nucleic acid construct with a sample, wherein the double-stranded functionalized nucleic acid constructs each comprises two binding partners having binding specificity for the same agent, and (b) detecting a change in conformation of the fully double-stranded functionalized nucleic acid construct from a linear to a looped conformation, wherein the change in conformation indicates presence of the agent.

In some embodiments, the change in conformation is detected using gel electrophoresis.

Another aspect of this disclosure provides a method comprising (a) contacting any of the foregoing fully double-stranded functionalized nucleic acid construct with a sample, wherein the double-stranded functionalized nucleic acid constructs each comprises two moieties, (b) detecting a change in conformation of the fully double-stranded functionalized nucleic acid construct from a linear to a looped conformation, wherein the change in conformation indicates binding of the two moieties to each other.

In some embodiments, the change in conformation is detected using gel electrophoresis.

In some embodiments, the method measures a rate of association or dissociation between the two moieties.

Another aspect of this disclosure provides a nucleic acid construct comprising a nucleic acid template hybridized to a capped blocking oligonucleotide, a reactive oligonucleotide, and a terminal 5' oligonucleotide. In some embodiments, the construct comprises two capped blocking oligonucleotides and two reactive oligonucleotides, wherein each reactive oligonucleotide is located immediately downstream of a capped blocking oligonucleotide, such that only a nick exists between the capped blocking oligonucleotide and the reactive oligonucleotide. In some embodiments, a polymerase such as a DNA polymerase is bound to the construct.

These and other aspects and embodiments of the invention will be described in greater detail herein.

DETAILED DESCRIPTION

This disclosure provides improved methods for generating nucleic acid nanoswitches, including fully double-stranded nucleic acid nanoswitches functionalized with one or more MOIs. The resultant fully double-stranded, nick-free nanoswitches have several advantages. First, by increasing the number of fully base-paired nucleotide monomers attached to a MOI, as is achieved by the nick-free nanoswitch of this disclosure, both the thermal stability of the nanoswitch and its resistance to applied force is significantly increased. Second, MOIs attached to a fully double-stranded nanoswitch have a considerably lower probability of non-specifically interacting with regions of single-stranded DNA. Such single-stranded DNA regions are more likely to occur using previous oligonucleotide tiling approaches, due to incompletely filled regions or oligonucleotides melting off the backbone as a function of the chemical (e.g., ionic) composition and/or the temperature of the solution. The opportunity for the MOI to interact with single-stranded DNA regions, while possible with earlier nanoswitch designs, has virtually been eliminated using the fully double-stranded design of this disclosure.

This disclosure provides several methods for generating double-stranded nanoswitches, such as fully double-stranded, nick-free nanoswitches. These are described below.

Covalent Filling of ssDNA Template Using a Polymerase and a DNA Ligase

Figure 1:
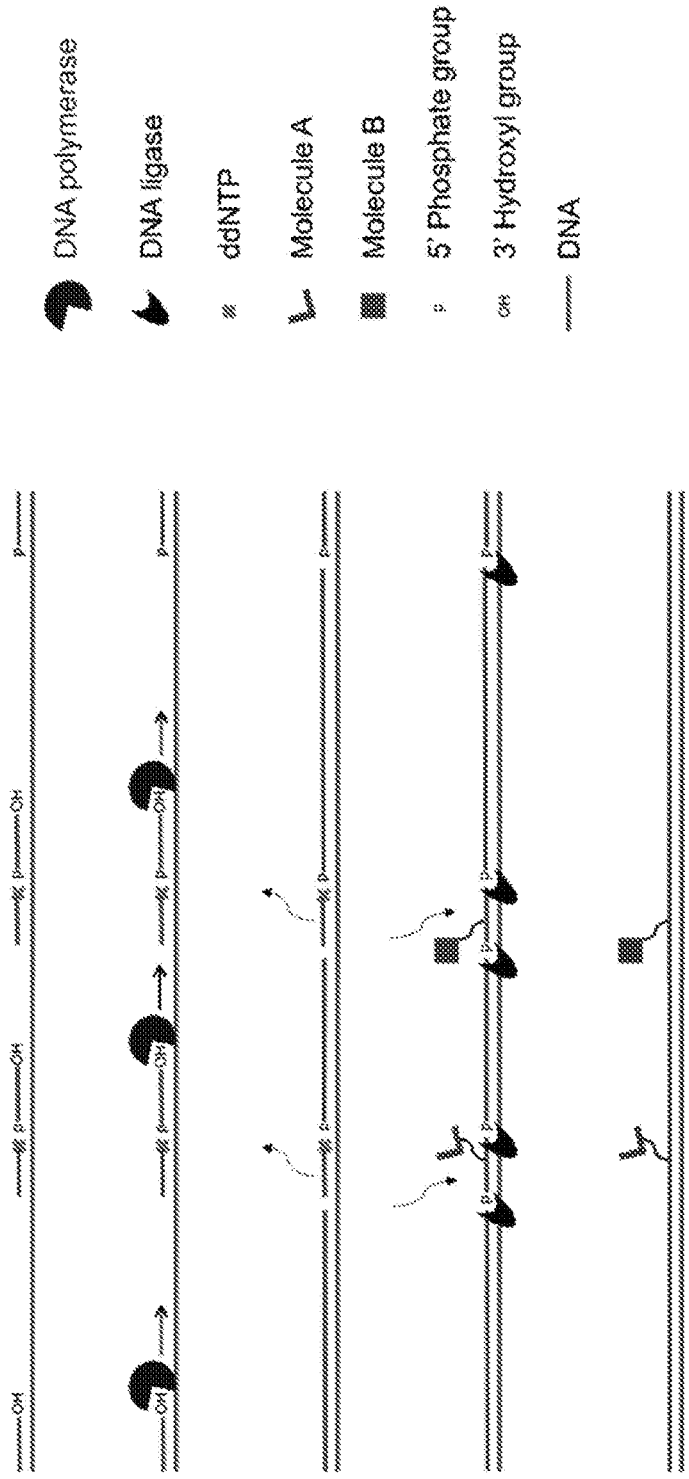
FIG. 1 shows target regions for nanoswitch functionalization blocked with non-reactive ("blocking") oligonucleotides having a terminal ddNTP, and the remainder of the template filled in with polymerization. The blocking oligonucleotide were then removed by heat denaturation, functionalized oligonucleotides were annealed, denoted as oligonucleotides conjugated to Molecule A or Molecule B, and the intervening gaps were sealed using a DNA ligase.

This method, which is shown in FIG. 1, relies on a joint nick repair and gap filling technique. Here, a small number of reactive oligonucleotides, including as few of 5-6 oligonucleotides, are annealed to the backbone nucleic acid (also referred to herein as a template nucleic acid and a scaffold nucleic acid), and the intervening space is filled in with a polymerase such as a DNA polymerase. The core of this method is the use of "blocking" oligonucleotides during polymerization. These blocking oligonucleotides are completely inert to ligation or polymerization. They function to block the site at which functionalized oligonucleotides (or oligonucleotides capable of being functionalized) will ultimately be annealed, and thus where MOI will be located. Following polymerization, these blocking oligonucleotides are removed to yield an intermediate construct that is completely double-stranded except for two short single-stranded regions where the blocking oligonucleotides were located. The length of either or both of these two regions is the length of the blocking oligonucleotides. Such length can be but is not limited to 15-150 nucleotides, including 19-60 nucleotides. The functionalized oligonucleotides (or oligonucleotides capable of being functionalized) can then be annealed at these locations and sealed into place with a DNA ligase.

As used herein, a functionalized oligonucleotide is one conjugated to an MOI. An oligonucleotide capable of being functionalized is one having the appropriate chemistry, group or moiety, all collectively referred to herein as a functionalization point, to which an MOI of interest may be attached. Such an oligonucleotide may be referred to herein as a functionalizable oligonucleotide. A functionalization point is a moiety, group or chemistry on a oligonucleotide to which an MOI is conjugated. Examples of functionalization points include internal primary amine groups, thiol groups, azide modifications, trans-cyclooctene (TCO) groups, benzylguanine (BG), benzylcytosine (BC), click chemistry partners, and the like. As an example, azide and TCO groups when used as functionalization points may be used to conjugate MOIs that are themselves functionalized with either a DBCO or methyl-tetrazine group using bifunctional linkers that also contain an amine reactive NHS ester group. Oligonucleotides capable of being functionalized may be considered to be modified oligonucleotides. It is to be understood that, while various of the embodiments described herein may be explained in terms of functionalized oligonucleotides, these teachings are intended to encompass functionalizable oligonucleotides as well, unless explicitly stated otherwise. The skilled person will understand that the difference between the use of these oligonucleotides involves an additional step of reacting a functionalization point with an MOI.

It is to be understood from the foregoing that oligonucleotides with functionalization points may also be annealed at these locations and sealed into place with a DNA ligase, and then such oligonucleotides may be functionalized (i.e., conjugated to an MOI) post-annealing, and optionally pre- or post-ligation. If MOI conjugation occurs after annealing, and if two or more different MOI are being attached to a single nanoswitch, then different functionalization points (e.g., different attachment strategies, different attachment chemistries, etc.) should be used to ensure proper placement of particular MOIs. The same attachment strategy or chemistry may be used to attach MOIs of a certain type, including identical MOIs, to an oligonucleotide, if so desired. But when different MOIs are to be attached to an oligonucleotide, this should be done using different attachment strategies or chemistries. For example, MOI A may be conjugated to functionalization point A' and MOI B may be conjugated to functionalization point B'.

This method minimally requires the single-stranded nucleic acid backbone, at least two reactive oligonucleotides, and one or more blocking (or inert) oligonucleotides (the number depending on how many functionalizations are desired on the ultimate nanoswitch). The method may further include oligonucleotides that bind to the 5' and/or 3' end of the backbone. These various classes of oligonucleotides are described in more detail below.

(1) Blocking oligonucleotides. One, two or more blocking oligonucleotides may be used in a synthesis method, depending on the desired number of MOIs. These oligonucleotides are complementary to the intended location of functionalization (i.e., the intended location of the MOI). The skilled person will be able to generate oligonucleotides that are complementary to a single region of a template of known sequence, whether such oligonucleotides are to be used as blocking oligonucleotides or reactive oligonucleotides or other oligonucleotides of this disclosure. Blocking oligonucleotides lack a 5' phosphate and therefore do not participate in polymerization or ligation. In some instances, they are also one nucleotide shorter (at their 3' end) than their counterpart functionalized oligonucleotide. In some instances, once the blocking oligonucleotides are annealed to the backbone, the intermediate construct so formed is contacted with a chain-terminating dideoxynucleotide (ddNTP) complementary to the unpaired nucleotide in the backbone (i.e., the ddNTP fills in the one nucleotide gap at the 3' end of the blocking oligonucleotide). The ddNTP may be provided as a mixture of ddNTP, or it may be provided as a single ddNTP type. ddNTP are nucleotides that contain a hydrogen group on the 3' carbon instead of a hydroxyl group (OH). The ddNTP is then joined to the 3' end of the blocking oligonucleotide either enzymatically, for example through the use of terminal deoxynucleotide transferase (TdT). TdT is a template-independent polymerase that catalyzes the addition of deoxynucleotides to the 3' terminus of DNA. Classically, TdT is used to add a homo- or heteropolymer chain of nucleotides to the 3' end of DNA, where the length of addition is dependent on the ionic composition and free nucleotide concentration in solution. In this disclosure, however, TdT can only add a single ddNTP to a 3' end of the blocking oligonucleotide because the incorporated ddNTP itself lacks a 3' hydroxyl group necessary for further addition. Each blocking oligonucleotide is therefore capped with only a single ddNTP. The blocking oligonucleotide capped at the 3' end with a ddNTP is referred to herein as a capped blocking oligonucleotide. The lack of a 5' phosphate and a 3' hydroxyl group on such capped blocking oligonucleotides renders them inert to DNA ligases and polymerases. These capped blocking oligonucleotides act as space-holders for functionalized oligonucleotides (or oligonucleotides capable of being functionalized) which are annealed and covalently joined to form a fully double-stranded construct later in the process.

In other instances, the blocking oligonucleotides may be generated synthetically by adding a ddNTP to the oligonucleotide during its synthesis (e.g., during phosphoramidite solid-phase synthesis). In these instances, the capped blocking oligonucleotide is designed to be fully complementary to its target sequence in the template and it is annealed to the template as is without involvement of TdT.

In still another instance, the blocking oligonucleotide is capped with a single ddNTP after oligonucleotide synthesis but prior to annealing to the template. The sequence of the template will be known and thus the sequence of the blocking oligonucleotide, including the ddNTP, will also be known. The oligonucleotide length and sequence is selected to be specific for a desired region of the backbone. The length of these oligonucleotides, in some embodiments, may be in the range of 10-250 nucleotides, or 10-200 nucleotides, or 50-200 nucleotides. Examples of blocking oligonucleotide sequences include but are not limited to

```
                                        (SEQ ID NO: 1)
CTGAACAAGAAAAATAATATCCCATCCTAATTTACGAGCATGTAGAAACC

AATCAATAAT
```
and
```
                                        (SEQ ID NO: 2)
TTGTTTAACGTCAAAAATGAAAATAGCAGCCTTTACAGAGAGAATAACAT

AAAAACAGGG.
```

Further examples of oligonucleotides that might be used as blocking oligonucleotides (provided their 3' end is a ddNTP) with a M13 backbone are provided in published PCT Application No. WO 2013/067489, the entire contents of which are incorporated by reference herein. If such blocking oligonucleotides were also used to block DNA ligation, then such oligonucleotides would also lack a 5' phosphate.

(2) Reactive oligonucleotides. The method typically requires at least one reactive oligonucleotide for every blocking oligonucleotide. FIG. 1 provides a schematic using two blocking oligonucleotides (denoted by the 3' "X") and two reactive oligonucleotides (denoted as having a 5' phosphate group and a 3' hydroxyl group). The reactive oligonucleotides may be positioned directly downstream of the 3' end of each capped blocker oligonucleotide. These oligonucleotides act as primers for polymerization and as substrates of ligation. The oligonucleotide length and sequence is selected to be specific for a desired region of the backbone. The length of these oligonucleotides, in some embodiments, may be in the range of 10-250 nucleotides, or 10-200 nucleotides, or 50-200 nucleotides. Examples of oligonucleotides that might be used as reactive oligonucleotides with a M13 backbone are provided in published PCT Application No. WO 2013/067489, the entire contents of which are incorporated by reference herein.

(3) Terminal oligonucleotides. The method may optionally include 5' and/or 3' terminal oligonucleotides. As their name implies, these oligonucleotides hybridize to the 5' or 3' terminal of the backbone, as illustrated in FIG. 1. One or both of the terminal oligonucleotides may be functionalized. For example, one or both may be functionalized for attachment to a support such as a solid support. This typically involves functionalization with an affinity molecule, provided such affinity molecule does not interfere with the MOIs ultimately presented by the construct. An example of such an affinity molecule is biotin or avidin, either of which may be used to anchor the construct to a support. Anchoring of the construct may be desirable if it is to be used in force spectroscopy measurements. The 3' terminal oligonucleotide may contain a 5' phosphate added either synthetically or by enzymatic phosphorylation. It may lack a 3' OH, in some instances. The 5' terminal oligonucleotide may lack a 5' phosphate, in some instances.

A typical method to generate a 2-MOI construct would comprise the single-stranded nucleic acid backbone, two blocking oligonucleotides (one for each MOI), two reactive oligonucleotides (e.g., one located immediately downstream of each blocking oligonucleotide), and a 5' terminal oligonucleotide. The 3' terminal oligonucleotide may be absent in some instances.

Polymerases that may be used in this and various other methods described herein include but are not limited to prokaryotic polymerases and eukaryotic polymerases, and include Pol I, Pol II, Pol III, Pol IV, Pol V, *E. coli* polymerase, Klenow fragment, Taq polymerase, T4 polymerase, T7 polymerase, Pfu polymerase, Vent polymerase, polymerases beta, lambda, sigma and mu, polymerases alpha, delta and epsilon, polymerases eta, iota and kappa, polymerase Rev1 and zeta, polymerases gamma and theta, polymerase nu, SpeedSTAR, PHUSION, Hot MasterTaq™, PHUSION Mpx, PyroStart, KOD, Z-Taq, and CS3AC/LA.

Ligases that may be used in this and various other methods described herein include but are not limited to prokaryotic ligases and eukaryotic ligases, and include *E. coli* DNA ligase, Taq DNA ligase, T4 DNA ligase, DNA ligase I, DNA ligase III, and DNA ligase IV.

Alternative annealing methods for creating a covalent double-stranded nanoswitch are also contemplated and described herein.

Tiling, Annealing and Ligation

In an alternative approach, the tiling process is used followed by ligation to create the double-stranded functionalized (or functionalizable) nucleic acid construct. First, all oligonucleotide tiles specific to filler regions (i.e., the non-functionalized regions) and optionally the functionalized 3' and 5' terminal oligonucleotides are annealed onto the backbone in DNA ligase buffer in a touchdown program. Each oligonucleotide is 5' phosphorylated with the exception of the terminal 5' oligonucleotide. Functionalized oligonucleotides with MOIs attached are then annealed isothermally (e.g., at 20 to 40° C.) onto the backbone. Then, a ligase such as for example Taq DNA ligase or T4 DNA ligase, is added to the mixture, and the nicks between each tiled oligonucleotide are sealed to create a fully double-stranded, functionalized nanoswitch.

Ligation-Dependent Joining of Functionalized dsDNA Fragments

This method generates interchangeable double-stranded nucleic acid fragments which can be directly functionalized and assembled by ligation to form a double-stranded nanoswitch. This method relies on an amplification reaction such as the polymerase chain reaction (PCR) for the production of each double-stranded building block. Two or more pairs of primers are used to amplify regions of interest from any template DNA including but not limited to M13 DNA. These primers are either already functionalized or they comprise functionalization points that will be functionalized with MOI following the amplification step. These resultant double-stranded nucleic acid blocks are then ligated together to create a functional nanoswitch.

Figure 3:
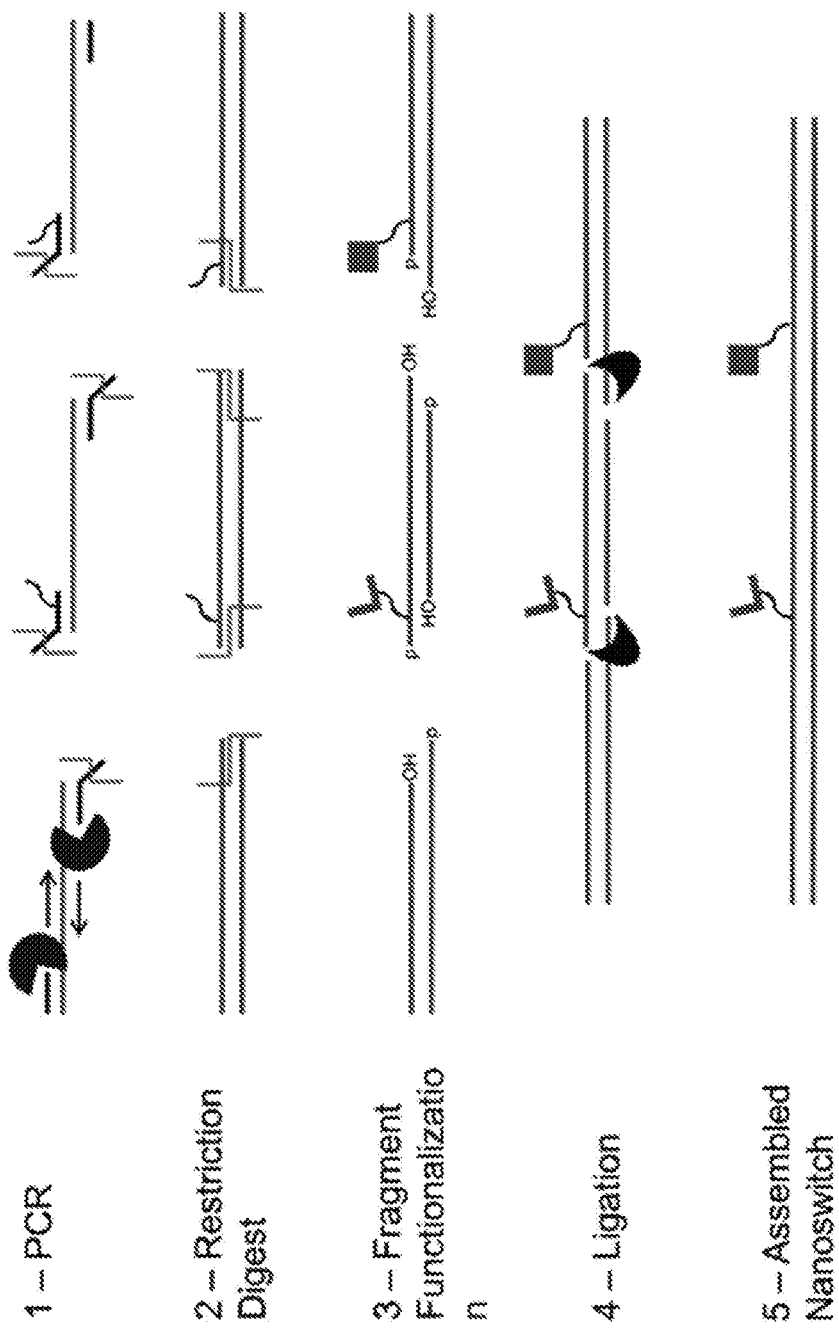
FIG. 3 shows three fragments amplified using three pairs of functionalized primers containing restriction enzyme site overhangs, and that are optionally functionalized (i.e., conjugated to an MOI such as molecule A or molecule B, as shown) or are capable of being functionalized (e.g., having appropriate chemistry to which an MOI may be attached). After digestion, functionalization and purification, the fragments were joined together using a DNA ligase.

This method is provided in FIG. 3. The Figure illustrates an exemplary embodiment comprising three pairs of primers and the resultant three double-stranded building blocks.

The left most double-stranded fragment is generated using a forward primer that may or may not be functionalized (e.g., for attachment to a solid support) and if not functionalized is typically de-phosphorylated, and a reverse primer that as illustrated has a site sequence overhang for restriction enzyme 1. The resultant fragment can then be digested using restriction enzyme 1 to yield a 5' overhang as illustrated. An example of a restriction enzyme that may be used for this first fragment is AgeI. In some instances, the reverse primer may also comprise a functionalization or a functionalization point (not shown in FIG. 3).

The middle double-stranded fragment is generated using a forward and a reverse primer, each having non-complementary restriction site sequence overhangs. In other words, the forward primer has a restriction site sequence overhang for enzyme 1 (i.e., the same enzyme used to cut the left-most double-stranded fragment) and the reverse primer has a restriction site sequence overhang for enzyme 2. An example of a restriction enzyme that may be used in conjunction with the reverse primer sequence is NotI. One or both of the forward and reverse primers for this second fragment may be functionalized or may comprise functionalization points. As illustrated, only the forward primer contains the functionalization point (as indicating by the curvy line attached to the primer).

The right-most double-stranded fragment is generated using a forward primer having a non-complementary restriction site sequence overhang for enzyme 2 and a functionalization point. The reverse primer contains either a functionalization to attach to a solid support, or is non-functionalized and de-phosphorylated.

The position and length of the primers, as well as the number of primer pairs to be used, will depend on the end user and the particular application, as well as the length of the template and the desired length of the nanoswitch.

The fragments so generated may be roughly similar in size although they are not so limited. In one embodiment, the first and third fragments may be on the order of about 1 kb in length while the second (middle) fragment may be on the order of about 500 bases in length.

It is to be understood that each of the fragments are generated separately from the others, restriction digested separately from the others, and then mixed following purification. In the example above, the first fragment would be digested with enzyme 1, the second fragment would be digested with enzymes 1 and 2, and the third fragment would be digested with enzyme 2. It is also to be understood that any combination of enzymes can be used provided that they generate the requisite complementary or non-complementary ends.

Next, fragments with functionalization points are subject to functionalization (i.e., conjugation to an MOI). MOIs may be attached to single- or double-stranded nucleic acids by any known means, including but not limited to SNAP-tag® chemistry. Each fragment may then be purified using for example either His-Tag affinity bead purification, or affinity purification followed by DNA purification using SPRI beads. Each purified potentially functionalized segment may be run on a gel next to the non-functionalized segment and checked to ensure that the fragment shifts upwards, indicating a change in molecular weight from the addition of the MOI.

Following purification, the fragments are combined together in equimolar concentrations in the presence of a ligase, and thereby attached to each other, to form a fully double-stranded nucleic acid construct.

In a variation of the foregoing, fragments with functionalization points are combined with the other double-stranded fragments in the presence of a ligase and are thereby attached to each other to form a fully double-stranded nucleic acid construct. In these instances, the MOI is attached to its particular functionalization point post-ligation rather than pre-ligation. In other words, the MOIs is attached to the double-stranded nucleic acid construct that is formed through this process rather than the shorter double-stranded fragment (building block). As described herein, if different MOI are being attached to the double-stranded nucleic acid construct, then the attachment strategy or chemistry (and thus the functionalization point) for each MOI should be orthogonal.

Amplification methods that may be used to generate the double-stranded nucleic acid building blocks for this method and/or to be used in other amplification steps described herein include but are not limited to polymerase chain reaction (PCR), rolling circle amplification (RCA), and isothermal amplification. Other amplification methods are known in the art and may be used in the methods provided herein.

Purification of the fragments or the final construct of this disclosure regardless of synthesis method may be performed using for example gel electrophoresis, affinity separation methods (using for example tags on fragments or oligonucleotides or nanoswitches), and DNA purification columns such as Zymo Select-a-Size DNA purification columns (Select-a-Size DNA Clean & Concentrator™).

Variations on the amplification method provided above are also contemplated as part of this disclosure. Such variations are described below.

Amplification Approach—Single Fragment

An alternative method for creating a covalent double-stranded nanoswitch for gel-based interaction assays involves the use of two primers, a forward and reverse primer, that target a template sequence of a length between 100 bp-100 kbp, and that are either pre-functionalized with MOIs or that contain functionalization points as defined herein. These functionalization points can be present, but are not limited to, at the 5' end of the primer or on a modified internal nucleotide. For example, a forward primer can contain a primary amine and a reverse primer can contain a thiol group for later attachment of MOIs via orthogonal chemistry. Alternatively, the forward primer can contain a 5' azide modification and the reverse primer can contain a 5' trans-cyclooctene (TCO) group. The fragment may be amplified using standard protocols. This reaction results in amplified fragments with two functional ends.

After the amplification step, the fragment of interest can be purified using a procedure such as but not limited to Zymo Select-a-Size DNA purification columns (Select-a-Size DNA Clean & Concentrator™) or purification from a gel.

As an example, if the primers comprise azide and TCO groups, MOIs such as two separate monoclonal antibodies can be attached by first functionalizing each antibody with either a DBCO or methyl-tetrazine group using bifunctional linkers that also contain an amine reactive NHS ester group. After reacting the respective bifunctional linker with the antibodies, excess linker can be removed, for example by performing one or more Zeba column desalting steps. The functionalized monoclonal antibodies will then be mixed in excess with the purified amplified fragments to form fragments conjugated to the antibodies. If needed, the functionalized nanoswitches can be purified from excess antibodies, using a procedure such as, but not limited to, Zymo Select-a-Size DNA purification columns (Select-a-Size DNA Clean & Concentrator™) or purification from a gel.

In any of the methods provided herein, the nanoswitches can be functionalized with two or more MOIs using alternative orthogonal chemical reactions, including but not limited to, benzylguanine (BG) modified oligonucleotide reacting with a SNAP-tags® protein and O2-benzylcytosine (BC) modified oligonucleotides reacting with a CLIP-tag™ protein. The effective concentration between the two MOI can be modulated by increasing or decreasing the length of the amplified PCR fragment.

As will be described in greater detail herein, the various functionalized nanoswitches generated according to the methods of this disclosure can be used in gel-based assays or other assay formats to obtain specific interaction measurements, on and off rate kinetics, and to detect an analyte in a sample (for example by using two sandwiching MOIs such as two sandwiching monoclonal antibodies).

Plasmid Approach

Still another method for creating a covalent double-stranded nanoswitch for gel-based interaction assays involves plasmids as a starting material. To create a nanoswitch from plasmids, in general terms, the plasmid is cut, for example using one or more restriction enzymes, and then the ends of the cut plasmid are functionalized, for example by ligating oligonucleotides functionalized with MOIs or having functionalization points (chemical groups, including orthogonal chemical groups, that can react with MOIs) using complementary sticky ends. As described herein, these orthogonal chemical groups include, but are not limited to, primary amine, thiol, azide, TCO, BG, and BC groups.

One exemplary procedure to create functionalized nanoswitches from plasmids is as follows: The base plasmid is designed to have a size of 50 bp-100 kbp and has two different restriction enzyme cut sites in close proximity to each other along the sequence. The plasmid is obtained and purified through traditional methods. The plasmid is cut with both restriction enzymes, to yield a longer linear strand with two non-complementary sticky ends (each end having been contributed by one of the restriction enzyme cut sites) and a shorter linear strand also with sticky ends. The longer linear strand can then be purified from the shorter linear strand and enzymes using a procedure such as but not limited to gel purification, or Zymo Select-a-Size DNA purification columns (Select-a-Size DNA Clean & Concentrator™)

Oligonucleotides that are either functionalized or capable of being functionalized can then be attached to the ends of the longer linear strand using ligation of sticky ends. These oligonucleotide will be double-stranded with one blunt end and a single-stranded region on the other end to create a complimentary sticky end. Here, two different sticky ends will be used to direct and properly place the different oligonucleotides on the ends of the longer linear strand in the presence of a ligase. These oligonucleotides can be created through direct chemical synthesis of single strands, including any chemical modifications, and followed by their hybridization to each other.

Nanoswitches that have functionalized oligonucleotides ligated to both ends can then be purified from free functionalized oligonucleotide constructs and non-ligated longer linear DNA using a techniques such as, but not limited to PAGE or agarose gel electrophoresis and purification. As described for the amplification approach, MOIs can be attached to the nanoswitches with functionalized chemical groups, and the nanoswitches can be purified from free proteins.

ssDNA Approach

In yet a further approach, nanoswitches can be constructed from a template such as but not limited to M13 in a manner similar to the tiling method described above. The difference is that instead of tiling the entire length of the single-stranded M13 construct with a plurality of non-functionalized oligonucleotides that effectively cover the majority of the M13 sequence, only 2 or more functionalized oligonucleotides comprising MOIs or functionalization points are used and thus tiled. Such minimally tiled nanoswitches are able to form linear and looped structures dependent on the presence (or absence) of their agent of interest. The degree of tiling, which may be represented as the percentage of nucleotides that are annealed, is greater than 0% and depending on the embodiment up to 10%, 20%, 30%, 40%, 50%, 60%, 70%, 80%, 90% or more. Looped constructs can be separated from unlooped constructs on a gel, similarly to fully tiled nanoswitches. In this case, to prevent extensive structure formation from interactions between regions of the single-stranded template, the gel can be run under conditions that disfavor strong DNA-DNA interactions. These conditions may include but are not limited to high voltage and use of formamide or urea in the sample and/or gel running buffer.

Nanoswitches Generally

A nanoswitch can exist in one of two conformational states: bound (closed, looped) or unbound (open, linear). As an example, a nanoswitch that comprises a pair of MOIs that are binding partners having specificity to each other (e.g., ligand and receptor) is in its open state if the binding partners do not bind to each other and the backbone nucleic acid remains linear. A nanoswitch is in its closed state if the binding partners bind to each other and the backbone nucleic acid forms a looped conformation.

In some embodiments, the nanoswitch is a fully double-stranded, nick-free nucleic acid comprising one, two or more MOI in particular (i.e., non-random) positions along its length.

In some embodiments, the nanoswitch is a partially double-stranded (and thus partially single-stranded) nucleic acid comprising two physically separate double-stranded regions (i.e., two double-stranded regions separated from each other by one single-stranded region, and one, two or more MOI attached to two double-stranded regions. Preferably, a single MOI is present at each double-stranded region.

In either nanoswitch conformation, it is further contemplated that a plurality of MOIs may be conjugated to the nanoswitch, at known (non-random) positions, and that such nanoswitches may be used to detect two or more agents simultaneously or sequentially. The nanoswitches of this disclosure may be used in analyte detection methods to detect one, two or more analytes. The MOIs may be arranged sequentially in the nanoswitch or they may be arranged in a nested manner provided that the conformation that is adopted upon binding of one agent (or analyte) can be distinguished from the conformation that is adopted upon binding of another agent (or analyte). Also, in some embodiments, the nanoswitch is designed such that binding of one analyte precludes binding to another analyte at the same time, while in other embodiments two or more analytes may be bound to the same nanoswitch at the same time without interference.

It is to be understood that in some contexts of this disclosure, the term agent is used to refer to a molecule of interest (MOI) that is conjugated to the nanoswitch, preferably covalently conjugated to the nanoswitch. In these contexts, the agent may be a binding partner that has binding specificity for an analyte such as protein or other component in a sample. In other contexts, the term agent is used to refer to the moiety being detected such as an analyte in a sample. The analyte in the sample may be a protein, such as early pregnancy factor, although it is not so limited.

The backbone (or template or scaffold) nucleic acid may be of any length sufficient to allow association (i.e., binding) and dissociation (i.e., unbinding) of MOIs such as binding partners to occur, to be detected, and to be distinguished from other events. In some instances, the backbone nucleic acid is at least 1000 nucleotides in length, and it may be as long as 20,000 nucleotides in length (or it may be longer). The backbone nucleic acid may therefore be 1000-20,000 nucleotides in length, 2000-15,000 nucleotides in length, 5000-12,000 in length, or any range therebetween. The backbone may be a naturally occurring nucleic acid (e.g., M13 DNA scaffolds such as M13mp18). M13 DNA scaffolds are disclosed by Rothemund 2006 Nature 440:297-302, the teachings of which are incorporated by reference herein. In some embodiments, including those involving a gel electrophoresis readout, the backbone nucleic acid may be at least 40, at least 50, at least 60, at least 70, at least 80, at least 90, at least 100, at least 200, at least 300, at least 400, at least 500, at least 600, at least 700, at least 800, or at least 900 nucleotides in length. The backbone nucleic acid may therefore be 100-1000 nucleotides in length, or 100-300 nucleotides in length, without limitation. In some embodiments, the backbone is about or less than 200 nucleotides in length. In some embodiments, the backbone and oligonucleotides are chosen and the MOIs are positioned to yield loops of about 40-100 base pairs. In some embodiments, it is important that the backbone nucleic acid is rendered single-stranded prior to annealing of oligonucleotides such as blocking oligonucleotides or reactive oligonucleotides or primers, etc. Methods for generating a single-stranded backbone include asymmetric PCR. The backbone nucleic acid may comprise DNA, RNA, DNA analogs, RNA analogs, or a combination thereof, provided it is able to hybridize in a sequence-specific and non-overlapping manner to the oligonucleotides. In some instances, the backbone nucleic acid is a DNA.

The backbone nucleic acid may be hybridized to 1, 2, 3, 4, 5, 6, 7, or more of oligonucleotides. With the exception of the methods described herein that employ blocking and reactive oligonucleotides, each of the oligonucleotides is able to hybridize to the backbone nucleic acid in a sequence-specific and non-overlapping manner (i.e., each oligonucleotide hybridizes to a distinct sequence in the backbone). The resulting constructs may comprise varying lengths of double-stranded regions. As a non-limiting example, 90% or more, including 95%, 96%, 97%, 98%, 99% and 100% of the backbone nucleic acid may be hybridized to oligonucleotides. It is to be understood that the double-stranded nucleic acid construct is typically also rendered nick-free through the use of a ligase post-annealing. The length and the number of oligonucleotides used may vary. It will be understood that the greater the length of the oligonucleotides, the fewer that may be needed to hybridize to the backbone nucleic acid, in some instances such as for example the full length tiling approach. In some instances, the length and sequence of the oligonucleotides is chosen so that each oligonucleotide is bound to the backbone nucleic acid at a similar strength. This is important if a single condition is used to hybridize a plurality of oligonucleotides to the scaffold nucleic acid. In some instances, the oligonucleotides are designed to be of approximately equal length. The oligonucleotides may be about 10, about 15, about 20, about 30, about 40, about 50, about 60, about 70, about 80, about 90, about 100, about 150, about 200, or about 250 nucleotides in length.

The number of oligonucleotides hybridized to a particular backbone may vary depending on the application. Accordingly, there may be 2 or more oligonucleotides hybridized to the backbone, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides. It will be understood that the number of oligonucleotides will depend in part on the application, the length of the backbone, and the length of the oligonucleotides themselves.

It is to be understood that the backbone nucleic acid and the oligonucleotides of the invention may be DNA or RNA in nature, or some combination thereof, or some analog or derivative thereof. The term nucleic acid refers to a polymeric form of nucleotides of any length, including deoxyribonucleotides, ribonucleotides, or analogs thereof. In some embodiments, the nucleic acids will be DNA in nature, and may optionally comprise modifications at their 5' end and/or their 3' end.

It is to be understood that, for convenience, the invention may refer to the oligonucleotides, nucleic acids, constructs and nanoswitches of this disclosure may be described as "DNA-based". These recitations are not to be construed as limiting the nature of the oligonucleotides, nucleic acids, constructs and nanoswitches to solely DNA. Accordingly, the DNA-based compositions of the disclosure are to be construed as exemplary embodiments only, unless stated otherwise.

In some embodiments, the MOIs may be binding partners and may include without limitation antibodies (or antibody fragments) and antigens, receptors and ligands, aptamers and aptamer receptors, nucleic acids and their complements, and the like.

In some embodiments, the first and second MOI are not nucleic acid in nature. In some embodiments, the first or the second MOI is nucleic acid in nature (e.g., it may be an aptamer) and the other MOI is not nucleic acid in nature. In some embodiments, the first and second MOI are both amino acid in nature (e.g., they may be peptides, proteins or protein fragments).

The number of nucleotides separating the MOIs is at least 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more nucleotides. In some embodiments, the distance is 40-100 nucleotides. Suitable distances will vary based on the application and will depend on the size of the MOIs, the degree of single- and double-strandedness of the looped region, the use of linkers to attach the MOIs to the nanoswitch, and the like.

The disclosure contemplates attachment of nanoswitches to a solid support. Such attachment may be covalent or it may be non-covalent in nature. In some embodiments, the nanoswitch comprises terminally located biotin and the solid support comprises avidin (including streptavidin). Alternatively, the nanoswitch may comprise terminally located avidin (including streptavidin) and the solid support may comprise biotin. In some embodiments, the solid support is a bead. It is not however so limited.

Methods of Use

The nanoswitches of this disclosure can be used in myriad applications, including for example, measuring the kinetics of molecular interactions, identifying molecular binding partners (from known or unknown candidates), analyte detection and associated diagnostic methods, and the like. Various applications are described below.

By functionalizing a nanoswitch with known or putative members of a binding pair, such as a receptor and a ligand, a single nanoswitch can be interrogated by force-extension, and binding pair interactions, such as receptor-ligand binding and unbinding, can be identified by a change in nanoswitch length or nanoswitch conformation. Additionally, under proper conditions the same pair of binding partners can be repeatedly bound and unbound. The approach is simple, versatile and modular, and can be easily implemented using standard commercial reagents and laboratory equipment. In addition to improving the reliability and accuracy of force measurements, this single-molecule nanoswitch paves the way for high-throughput serial measurements, high-throughput identification of binding partners for targets of interest, single-molecule on-rate and off-rate studies, investigations of population heterogeneity, detection of analytes in samples and diagnostic applications relating thereto.

In these and other embodiments, the identity of the first and/or second MOI on a nanoswitch may be known or unknown. In some instances, the identity of one may be known (e.g., it may be a target of interest) and the identity of the other may be unknown (e.g., it may be a member of a library that is being screened). In some instances, the identity of both may be known, and the methods may be used to measure binding strengths, rates of association or dissociation between the two under static or changing conditions, or it may be used to identify another agent that interferes with or enhances binding between the first and second MOI.

In some embodiments, one MOI is a member of a library of putative binding partners and the method is intended as a screening method to identify binding partners with affinity for a particular target (i.e., the other MOI) or as a comparison of a plurality of putative or known binding partners based on affinity. Accordingly, in some embodiments, the MOIs are known to have affinity for each other, while in other embodiments, it may not be known prior to the assay whether they have affinity for each other, or the degree of affinity (i.e., the binding strength) in a given pair may not be known. In some embodiments, association and dissociation kinetics may be determined by detecting conformational changes in nanoswitches over a span of time, optionally under one or a variety of conditions. Conformational changes may be detected using techniques known in the art including those described herein.

In still other embodiments, the two MOIs are binding partners for the same agent (e.g., an analyte of interest in a diagnostic or detection assay). The MOIs may be identical to each other provided they can both bind simultaneously to the agent, or they may be different from each other yet still bind to the same agent. As an example, both MOI may be antibodies or antigen-binding antibody fragments.

In some embodiments, the first MOI is a receptor and the second MOI is a ligand of the receptor. In some embodiments, the first MOI is an antibody or an antigen-binding antibody fragment and the second MOI is an antigen (or an epitope-bearing antigen fragment) that is recognized and bound by the antibody or antibody fragment. In some embodiments, the first MOI is a hapten and the second MOI is a hapten binding partner. In some embodiments, the first MOI is a lectin and the second MOI is a lectin-binding moiety such as a carbohydrate. It is to be understood that the MOI may be used in an isolated form (e.g., physically separate from components or moieties with which they naturally occur). In some embodiments, they may be bound to a support such as a cell (e.g., a cell surface receptor or ligand).

Change in binding including presence or absence of binding, and/or change in conformational state in any of the aspects and embodiments of the disclosure, may be detected using any suitable methodology including but not limited to gel electrophoresis, single-molecule force probes such as optical tweezers, magnetic tweezers, atomic force microscopy (AFM), centrifuge force microscopy (CFM), tethered particle motion, and single-molecule fluorescence imaging.

In some embodiments, photoactive or non-photoactive crosslinking agents can be used to fix or freeze a particular nanoswitch conformation. As an example, a photoactive crosslinker such as psoralen may be used to preserve nanoswitch conformations at different times prior to sampling the nanoswitches. Cros slinking provides a "snapshot" of how much of the nanoswitch is in a bound/closed state at any given time and may be necessary to preserve the conformation in instances where the interaction kinetics are faster than the observation time such as the gel running time.

Competitive Binding Assays to Measure Molecular/Chemical Kinetics.

The nanoswitches provided herein may be used in methods of measuring the kinetics of molecular interactions. By monitoring the change in states from open to closed and vice versa, the kinetics of the binding interaction between the MOIs such as binding partners can be determined. In some embodiments, the conformational state can be resolved on an electrophoretic gel or using any of the foregoing methodologies.

The following protocol can be used to measure the kinetics (e.g., off-rate) of molecular binding partners on a nanoswitch: 1) providing a nanoswitch that comprises two binding partners (e.g., A and A') bound to each other (i.e., in a closed conformation), 2) add excess of a soluble form of one binding partner (A) that will bind to its binding complement (A') when the A-A' bound to the nanoswitch dissociate from each other, essentially fixing the dissociated nanoswitch in an open conformation, 3) determine the conformational state of the nanoswitches over a period of time in order to determine the off-rate of the A-A' interaction. With time, the closed conformation will convert to the open conformation. The rate at which that conversion occurs is an indicator of the strength of binding between those binding partners. The soluble form of the binding partner (A) may be present at a 2-fold, 3-fold, 5-fold, 10-fold, 50-fold, 100-fold, or more excess over the amount (or concentration) of the complex-bound form of the binding partner (A).

Internal Mechanical Force as a Measure of Force-Dependent Kinetics.

The nanoswitches provided herein may be used in methods of measuring force-dependent kinetics of binding interactions by creating a force that is internal to the nanoswitch (rather than applying an external force as can be done using optical tweezers or magnetic tweezers, for example). This method takes advantage of "internal" mechanical forces that are created when a double-stranded nucleic acid is circularized. (Shroff et al. *Biophysical Society* (2008) 94:2179-86) Changing the length of a nucleic acid loop varies the internal force of the complex, with force increasing as the length decreases. For example, binding partners on a backbone nucleic acid that are separated by approximately 200 to 300 nucleotides will easily bind to form a closed loop configuration because there is very little, if any, internal force created by the loop. On the other hand, the same binding partners when separated by shorter distances will less readily form a closed loop conformation (and when formed, may more readily dissociate) as the force imposed by the backbone nucleic acid approaches, is similar to, and/or exceeds the binding strength between the binding partners.

The following protocol can be used to measure the force-dependent kinetics of binding partners on a nanoswitch: 1) provide a plurality of nanoswitches, each nanoswitch within the plurality comprising the same binding partner pair, wherein the number of nucleotides separating the binding partners on a backbone nucleic acid varies within the plurality, and 2) determine the presence of bound versus unbound nanoswitches as a function of separating distance, using for example gel electrophoresis. It is expected that as the loop length decreases, the ratio of bound to unbound nanoswitches will decrease also. In some embodiments, the protocol can include the initial formation of a loop that predominantly consists of single-stranded DNA, as may be accomplished using the ssDNA methods provided herein. To generate tension within these loops, oligonucleotides complimentary to portions of the looped backbone regions are added and allowed to hybridize to the backbone, thereby generated a mechanical force upon hybridization and formation of double-stranded regions within the loop. The force can be therefore be precisely and finely varied in time and magnitude by varying the amount of double-stranded versus single-stranded nucleic acid in the loop. (Shroff, Liphardt et al., Nano Letters 2005.)

Analyte Detection.

Some aspects of this disclosure provide methods for detecting the presence of an analyte of interest in a sample using the nanoswitches described herein. In these aspects, the nanoswitch comprises two binding partners that have specificity for the same analyte. The binding partners may be identical to each other, provided that they can both bind to the analyte simultaneously. As an example, they may be identical antibodies provided the antigen to which they bind has several epitopes that can be bound by the antibodies simultaneously without interference. The binding partners may be different from each other but have binding affinity for the same analyte. As an example, they may be antibodies that bind to different epitopes on the same antigen provided they can bind to the antigen simultaneously without interference. The bound and unbound conformation of the nanoswitch can be used to determine the presence and absence of an analyte in a sample, respectively. If the analyte is present, the binding partners will bind to the analyte and the nanoswitch will form a closed loop conformation. In the absence of the analyte, binding will not occur, and the complex will remain open.

The following protocol can be used to detect an analyte in a sample: 1) combine a sample with a nanoswitch comprising binding partners of the analyte (e.g., antibodies to the analyte), and 2) determine the conformation of the nanoswitch for example by gel electrophoresis. Detection of a closed loop conformation is an indication that the analyte is present in the sample and binds to the two binding partners.

Screening Methods and Identification of Binding Partners.

Some aspects of this disclosure provide methods for screening a plurality of binding partners for a target binding partner using the nanoswitches described herein. By attaching a known moiety and a candidate binding partner to different regions of the nanoswitch, and determining whether a looped conformation is formed between the two, a binding partner to the known moiety can be identified. If the candidate binding partner is a true binding partner of the known moiety, then it will bind to the known moiety, and the complex will form a closed loop conformation. If the candidate binding partner has virtually no affinity for the known moiety, the complex will remain open. The method can be used to evaluate the binding specificity and affinity of a variety of candidate molecules including those that are nucleic acid in nature, such as aptamers, and those that are amino acid in nature such as peptides proteins including antibodies and antibody fragments.

The following protocol can be used to screen for binding partners on a nanoswitch: 1) provide a collection of nanoswitches that comprise a known moiety (e.g., a target molecule) and a unknown candidate binding partner (e.g., a member of a library), and 2) determine the conformation of the nanoswitch at one or more times for example by gel electrophoresis. Detection of a closed loop conformation is an indication that the candidate binding partner has affinity for the known moiety. It is also possible to order a number of candidate binding partners based on their degree of affinity for the known moiety. In other embodiments, the conformational state can be resolved using any of the methodologies described herein.

Various uses and applications of nanoswitches are described in published applications US 2014/0255939 published Sep. 11, 2014 and WO2016/089588 published Jun. 9, 2016, the entire contents of which are incorporated by reference herein.

EXAMPLES

Example 1. Covalent Filling of ssDNA Template Using a Polymerase and a DNA Ligase Materials and Methods The following synthetic oligonucleotides were annealed in a touch down program in a thermocycler onto the ssDNA template—M13mp18 single-stranded DNA (New England Biolabs, N4040S)—in 10× molar excess in low salt buffer, typically 90° C. to 20° C. at 0.1-1° C. $\text{min}^{-1}$:
 (1) One oligonucleotide complementary to the distal 5' end of the template.
 (2) Two blocking oligonucleotides complementary to the intended functionalized target location, which both lack a 5' phosphate and contain a 3' ddNTP added either during phosphoramidite solid-phase synthesis or by addition by TdT post-synthesis and either pre-annealing or post-annealing to the template. These oligonucleotides do not participate in polymerization or ligation.
 (3) Two reactive oligonucleotides directly downstream of the 3' end of each blocker oligonucleotide (including 3' ddNTP), each 5' phosphorylated.

Figure 2:
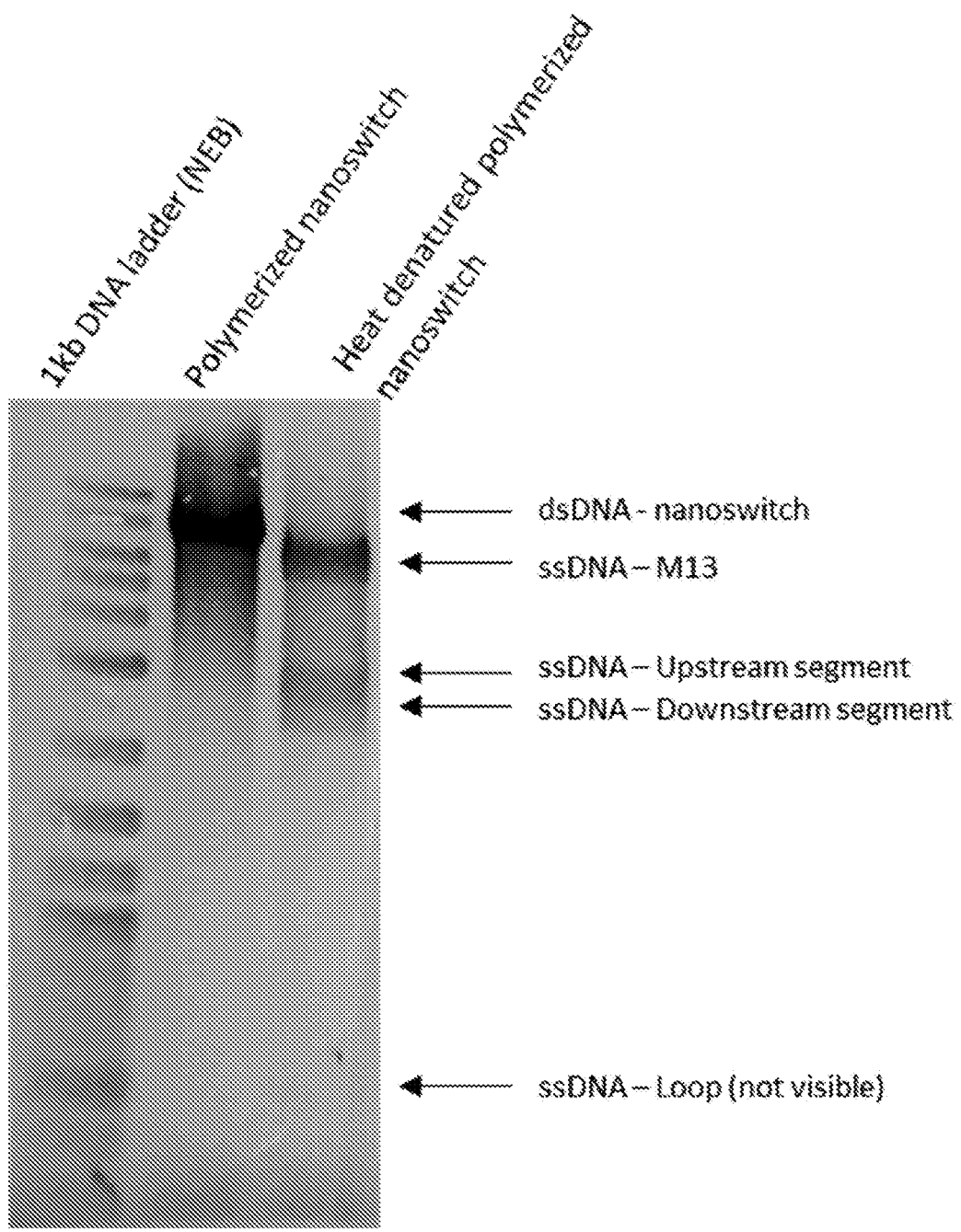
FIG. 2 shows a polymerized nanoswitch created using the method of Example 1. To demonstrate specific polymerization of each segment, the nanoswitch was heat denatured at 95° C. for 2 minutes, then snap cooled on ice. Each nanoswitch was run on a 1% agarose gel in TAE buffer for 1 hour at 5 V/cm. Lane 1 was a 1 kb DNA ladder (NEB). Lane 2 was the polymerized nanoswitch made using two blocking oligonucleotides, as shown in FIG. 1. Lane 3 was the nanoswitch from lane 2 subjected to heat denaturation. The small loop segment is not visible on this image due to low exposure settings. The loop segment represents the segment between the functionalization sites. The length of this segment will dictate the length or size of the loop created upon binding of the nanoswitch to its target by the two functionalization sites.

The oligonucleotides were annealed to the backbone, the solution was mixed with a 2× Q5 DNA polymerase Master Mix (NEB), and then placed in a thermocycler. The temperature was raised to 72° C. for 7 minutes to allow for complete polymerization and gap filling, and was then chilled to 4° C. Oligonucleotides complementary to the blocking oligonucleotides were then added in 5× molar excess to the blocking oligonucleotides. EDTA was also added to a final concentration of 20 mM to inhibit further polymerization. The temperature was then raised to 5-15° C. above the calculated melting temperature ($T_m$) in Q5 polymerase buffer, typically between 75-85° C. for 5 minutes, then cooled to room temperature. This step ensures that all of blocker oligonucleotides are removed from the template, and will not re-anneal. Next, the DNA template containing the two gaps was purified from excess oligonucleotides, enzyme, and buffer components using the Zymo Select-a-Size DNA purification columns (Select-a-Size DNA Clean & Concentrator™). The cutoff size selected was >300 bp ssDNA to ensure complete removal of primers. The DNA was then eluted in 10 mM Tris-HCl buffer, pH 8.0. FIG. 2 is a photograph of the gel electrophoresis results showing the polymerized nanoswitch and its components upon heat denaturation including the single-stranded M13 template, and the "upstream and downstream segments" which correspond to the single stranded segments polymerized from the single stranded reactive oligonucleotides. The "loop" is the middle segment of polymerized nucleic acid that corresponds in length to the loop which can be formed if two reactive moieties are functionalized to the nanoswitch and then bound to an identical target.

Next, functionalized oligonucleotides containing low secondary structure were mixed with the polymerized template DNA in a 1-5 molar excess, and diluted to a 1× concentration with Taq or T4 DNA ligase buffer (NEB). The annealing temperature was determined by choosing a temperature where the minimum free energy structure of the oligonucleotide is in its linear form in the specific buffer chosen, based on calculations performed in NUPACK software (Zadeh, 2011).

To repair gaps, either Taq or T4 DNA ligase enzyme (NEB) was used. When Taq DNA ligase was used, the enzyme was added to the mix, and the oligonucleotides were annealed and ligated into place in a thermocycler for 1 hour at 30-37° C. for 1 hour. For T4 DNA ligase, the mix without enzyme was incubated for 1 hour at 37° C., then cooled to room temperature. Enzyme was added and then incubated for 10 minutes at room temperature. The use of T4 DNA ligase requires that the distal ends of the nanoswitch are blocked due to the ability of this enzyme to ligate blunt ends together. Therefore, the distal 3' and 5' ends of the DNA should be blocked either by de-phosphorylation using an alkaline phosphatase such as CIP(NEB) or by the addition of functional groups attached via the exposed phosphate groups.

Example 2. Ligation Dependent Joining of Functionalized dsDNA Fragments

Materials and Methods

First, three sets of forward and reverse PCR primers were synthesized. Each set targets a specific block of M13 DNA, or other template DNA.

The first pair of primers has a forward primer that is either 5' functionalized for attachments to solid supports, or non-functionalized and de-phosphorylated, and a reverse primer that has a restriction site sequence overhang (e.g., specific for AgeI). The reverse primer may further comprise a functionalization point, if desired.

The second pair of primers has a forward primer that has a restriction site sequence overhang (e.g., specific for AgeI) and a functionalization point (e.g., an internal primary amine group). The reverse primer of this pair contains a non-complementary restriction site sequence overhang (e.g., specific for NotI).

The third pair of primers contains a forward primer with a non-complementary restriction site sequence overhang (e.g., specific for NotI) and a functionalization point (e.g., an internal primary amine group). The reverse primer of this pair contains either a functionalization point to attach to a solid support, or is left non-functionalized and de-phosphorylated.

Exemplary nucleotide sequences for these forward and reverse primers are as follows:

```
                                              (SEQ ID NO: 3)
    F1: GAAAGGCCGGAGACAGTCAAATC (SEQ ID NO: 4)
    R1: GTTATTACCGGTCCAATACGCAAACCGCCTCTC (SEQ ID NO: 5)
    F2: TATTGGACCGGTAATAACGGATTCGCCTGATTGC (SEQ ID NO: 6)
    R2: CTTATGCCATGGACGCCTTATTTATCACACGGTCG (SEQ ID NO: 7)
    F3: AGGCGTCCATGGCATAAGGGAACCGAACTGACCAAC (SEQ ID NO: 8)
    R3: GAATTGATGCCACCTTTTCAGCTC
```

In this example, these primer sets will generate three separate fragments (#1-3). Fragments 1 and 3 are the end fragments and each is ~1 kb in length, while fragment 2 is the loop fragment and is ~500 bp in length.

The described sets of primers were used in a PCR reaction using Q5 DNA polymerase 2× Master Mix (NEB) and template DNA at 10 pg/uL-1 ng/uL. In this example, the template (i.e., backbone) DNA is M13 single-stranded DNA. It is to be understood that any nucleic acid of known sequence may be used as the template including single- and double-stranded nucleic acids. The solution was placed in a thermocycler and was subjected to the following protocol:

| | |
|---|---|
| 1. 98° C. | 1:00 |
| 2. 98° C. | 0:07 |
| 3. 64° C. | 0:30 |
| 4. 72° C. | 0:30 |
| 5. 72° C. | 2:00 |
| 6. 4° C. | Hold |
| Cycle step 2-4: 35× | |

After the PCR reaction completed, each mixture was column purified using silica columns (Zymo Research, DCC-25). Next, each mixture was measured for concentration using a Nanodrop (Thermo Scientific), and 1 nanogram was run on a 1.5% agarose gel to check for the correct size product. Next, each PCR product was subjected to a restriction digest, using AgeI for Segment 1, AgeI+NotI for Segment 2, and NotI for Segment 3. Each reaction was then column purified again using the DCC-25 columns.

Next, Segments 2 and 3 were subjected to functionalization, if not already pre-functionalized. Here, MOIs were attached using SNAP-tag® chemistry. Each segment was then purified by either His-Tag affinity bead purification, or affinity purification followed by DNA purification using SPRI beads. Each purified segment was run on a gel next to the non-functionalized segment and checked to ensure that the fragment shifts upwards, indicating a change in molecular weight from the addition of the MOI.

Finally, each fragment was mixed together in equimolar concentrations and T4 DNA ligase buffer (NEB) was added to a 1× concentration. Next, T4 ligase enzyme (NEB) was added, and the ligation reaction was allowed to proceed for 10-30 minutes at room temperature, or for 4 hours at 16° C. The constructed nanoswitch was then run on a gel to confirm that was completely ligated.

Excess ligase can be removed either by affinity purification against the ligase, through dialysis membranes with a high molecular weight cutoff (MWCO), through MWCO columns, which will pass the ligase through, but leave the large nanoswitch in the supernatant, or via gel purification if compatible.

Example References

1. Halvorsen, K., Schaak, D. & Wong, W. P. Nanoengineering a single-molecule mechanical switch using DNA self-assembly. *Nanotechnology* 22, 494005 (2011).
2. Zadeh, J. N. et al. NUPACK: analysis and design of nucleic acid systems. *Journal of computational chemistry* 32, 170-173 (2011).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used.

Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising
amplifying a sequence from a template nucleic acid using a forward and a reverse primer, thereby generating a double-stranded nucleic acid fragment, wherein the forward and the reverse primers are functionalized with binding partners that bind to a common analyte, wherein the binding partners on the forward and reverse primers are not identical and are independently selected from the group consisting of a receptor, a ligand of a receptor, an antibody, an antigen-binding antibody fragment, an antigen, an epitope-bearing antigen fragment, a lectin, and a lectin-binding moiety.

2. A method comprising
(a) amplifying a sequence from a template nucleic acid using a forward and a reverse primer, thereby generating a double-stranded nucleic acid fragment, wherein one of the primers is functionalized with a binding partner that binds to another binding partner or to an analyte, and the other primer has a functionalization point that comprises a moiety, group, or chemistry to which a molecule of interest may be conjugated, and (b) functionalizing the double-stranded nucleic acid fragment using the functionalization point, thereby forming a fully double-stranded functionalized nucleic acid construct.

3. The method of claim 2, wherein one of the primers is functionalized with a binding partner that binds to another binding partner and the other primer has a functionalization point that comprises a moiety, group, or chemistry to which a molecule of interest may be conjugated.

4. The method of claim 3, wherein the functionalization point is selected from an internal primary amine group, a thiol group, an azide modification, a trans-cyclooctene group, a benzylguanine, a benzylcytosine, and a click chemistry partner.

5. The method of claim 2, wherein one of the primers is functionalized with a binding partner selected from the group consisting of a receptor, a ligand of the receptor, an antibody, an antigen-binding antibody fragment, an antigen, an epitope-bearing antigen fragment, a lectin, and a lectin-binding moiety.

* * * * *

SEQUENCE LISTING

<160> NUMBER OF SEQ ID NOS: 8

<210> SEQ ID NO 1
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 1
ctgaacaaga aaataatat cccatcctaa tttacgagca tgtagaaacc aatcaataat       60

<210> SEQ ID NO 2
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 2
ttgtttaacg tcaaaaatga aaatagcagc ctttacagag agaataacat aaaaacaggg       60

<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
gaaaggccgg agacagtcaa atc       23

<210> SEQ ID NO 4
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 4
gttattaccg gtccaatacg caaaccgcct ctc       33

<210> SEQ ID NO 5
<211> LENGTH: 34

```
<212> TYPE: DNA
<213> ORGANISM: Artificial Sequence
<220> FEATURE:
<223> OTHER INFORMATION: Synthetic polynucleotide

<400> SEQUENCE: 5
tattggaccg gtaataacgg attcgcctga ttgc                              34

<210> SEQ ID NO 6
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 6
cttatgccat ggacgcctta tttatcacac ggtcg                             35

<210> SEQ ID NO 7
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 7
aggcgtccat ggcataaggg aaccgaactg accaac                            36

<210> SEQ ID NO 8
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 8
gaattgatgc cacctttca gctc                                          24
```